United States Patent
Ruedinger et al.

(10) Patent No.: US 6,692,706 B2
(45) Date of Patent: Feb. 17, 2004

(54) PROCESS FOR PREPARING SATURATED CARBOXYLIC ACIDS HAVING FROM 1 TO 4 CARBON ATOMS

(75) Inventors: Christoph Ruedinger, München (DE); Hans-Juergen Eberle, München (DE); Ragnar Bogner, München (DE); Wolfgang Kohlmann, München (DE)

(73) Assignee: Consortium für elekrochemische Industrie GmbH, Munich (DE)

(*) Notice: Subject to any disclaimer, the term of this patent is extended or adjusted under 35 U.S.C. 154(b) by 0 days.

(21) Appl. No.: 10/167,513

(22) Filed: Jun. 12, 2002

(65) Prior Publication Data

US 2002/0177734 A1 Nov. 28, 2002

Related U.S. Application Data

(62) Division of application No. 09/313,400, filed on May 18, 1999.

(30) Foreign Application Priority Data

May 22, 1998 (DE) .......................................... 198 23 088
Mar. 10, 1999 (DE) .......................................... 199 10 628

(51) Int. Cl.[7] .............................. C07C 51/16; B01J 8/04
(52) U.S. Cl. ....................... 422/196; 422/198; 422/201; 422/211; 562/549
(58) Field of Search ............................ 562/549, 512.2, 562/523, 546, 547, 548, 607; 422/196, 198, 201, 211

(56) References Cited

U.S. PATENT DOCUMENTS

| | | |
|---|---|---|
| 3,431,297 A | 3/1969 | Brockhaus |
| 3,565,829 A | 2/1971 | Friedrichsen et al. |
| 3,704,317 A | 11/1972 | Yamashita et al. |
| 3,917,682 A | 11/1975 | Mizukami et al. |
| 3,948,983 A | 4/1976 | Hachmann et al. |
| 4,146,734 A | 3/1979 | Slinkard |
| 4,158,740 A | 6/1979 | Lese et al. |
| 5,750,777 A * | 5/1998 | Aubry et al. ............ 562/512.2 |
| 6,320,075 B1 * | 11/2001 | Ruedinger et al. ....... 562/512.2 |

FOREIGN PATENT DOCUMENTS

| | | |
|---|---|---|
| DE | 1279011 | 7/1964 |
| DE | 1279011 | 10/1968 |
| DE | 1921503 | 11/1969 |
| DE | 2149752 | 4/1972 |
| DE | 2149752 | 6/1980 |
| DE | 19649426 | 6/1998 |
| EP | 0546 677 | 10/1992 |
| GB | 1010058 | 10/1962 |
| GB | 1165442 | 10/1969 |
| GB | 1356331 | 6/1974 |

OTHER PUBLICATIONS

R.P. Lowry, A. Aguilo, Hydrocarbon Processing, 10, (1974), 103.
PEP Report No. 37 A, (1973).
Derwent Abstract (# 1998–313425 [28]) corresponding to DE 19649426.

* cited by examiner

Primary Examiner—Alan L. Rotman
Assistant Examiner—Taylor V. Oh
(74) Attorney, Agent, or Firm—Collard & Roe, P.C.

(57) ABSTRACT

A process for preparing saturated carboxylic acids having from 1 to 4 carbon atoms at a reaction temperature of from 100° C. to 400° C. and pressures of from $1.2 \times 10^5$ Pa to $51 \times 10^5$ Pa by gas phase oxidation of saturated and/or unsaturated $C_4$-hydrocarbons, with an oxygen-containing gas and water vapor in the presence of at least one catalyst. The gas leaving the reactor is partly recirculated in a reaction gas circuit. This reaction gas circuit is configured such that part of the organic acids formed in the gas-phase oxidation is taken from the gas leaving the reactor so that the acid content of the recirculated part of the gas leaving the reactor is from 0.01% to 6.0% by volume.

10 Claims, 3 Drawing Sheets

PROCESS FOR PREPARING SATURATED CARBOXYLIC ACIDS HAVING FROM 1 TO 4 CARBON ATOMS

CROSS-REFERENCE TO RELATED APPLICATIONS

Priority is claimed under 35 U.S.C. 119 of German Patent Application No. 198 23 088.5 filed May 22, 1998, and German Patent Application No. 199 10 628.2 filed Mar. 10, 1999. Priority is claimed under 35 U.S.C. 120 of parent U.S. patent application which is a divisional of Ser. No. 09/313,400 filed May 18, 1999, with this application being a divisional patent application thereof.

BACKGROUND OF THE INVENTION

1. Field of the Invention

The present invention relates to a process for preparing saturated carboxylic acids having from 1 to 4 carbon atoms and to an apparatus for carrying out this process.

2. The Prior Art

It is known that acetic acid can be prepared by gas-phase oxidation of $C_4$-hydrocarbons in the presence of a catalyst. Most prior art processes provide for the reaction gas mixture to be passed over the catalyst once, to separate off the resulting acetic acid by condensation or scrubbing and to discard the remaining gas. For example, U.S. Pat. No. 3,917,682 describes a procedure in which the acetic acid is obtained by oxidation of butene in the presence of a Ti/V catalyst having a high proportion of rutile. Here the acetic acid is isolated by partial condensation of the reaction mixture and the remainder of the reaction gas is not recirculated. Such processes have to achieve a high butene conversion on a single pass through the reactor, which can be achieved only at low yields or low space-time throughputs. For this reason, an economically satisfactory process has not yet been developed on the basis of this process concept.

It is known from U.S. Pat. No. 4,146,734 that the gas-phase oxidation of butene to acetic acid can be carried out in the presence of a catalyst comprising lanthanide compounds. A method of isolating the acetic acid and further desired compounds formed during the gas-phase oxidation is not indicated.

DE-A 2,149,752 and DE-A 1,279,011 describe processes for the catalytic gas-phase oxidation of butene to acetic acid in the presence of specific catalysts. A disadvantage of these processes is that the formic acid formed as desirable compound decomposes during the recirculation of the noncondensable part of the reaction gas.

DE-A 1,921,503 refers to the possibility of, in the preparation of acetic acid by catalytic gas-phase oxidation of butene, recirculating the unreacted part of the reaction mixture to the reactor. However, express reference is made to the uneconomical nature of a circulating gas process.

The process was developed to the pilot plant scale by Chemische Werke Hüls and is described in various publication (R. P. Lowry, A. Aguilo, *Hydrocarbon Processing*, 10, (1974), 103; PEP Report No. 37A (1973)). It provides for the direct, untreated recirculation of ⅘ of the gas mixture leaving the reactor (FIG. 1). In this embodiment, the reaction product is partly circulated without the acids being separated off and only part is taken off for isolation of acetic acid. In this process, there is significant accumulation of organic acids in the reaction gas, as a result of which both acetic acid and formic acid are obtained only in unsatisfactory yield.

SUMMARY OF THE INVENTION

It is an object of the present invention to provide a process for preparing saturated carboxylic acids having from 1 to 4 carbon atoms, in particular acetic acid, by gas-phase oxidation of saturated and/or unsaturated $C_4$-hydrocarbons, which gives high acid yields and in which the by-products are obtained as useful materials.

It has surprisingly been found that the preparation of saturated carboxylic acids having from 1 to 4 carbon atoms by gas-phase oxidation of saturated and/or unsaturated $C_4$-hydrocarbons can be carried out with particularly high yields. These high yields will result if, in contrast to the above-mentioned prior art processes, a substream which has been substantially freed of acids, of the gas mixture leaving the reactor, is recirculated to the reactor inlet.

The present invention provides a process for preparing saturated carboxylic acids having from 1 to 4 carbon atoms by gas-phase oxidation at a reaction temperature of from 100° C. to 400° C. and pressures of from $1.2 \times 10^5$ Pa to $51 \times 10^5$ Pa. This oxidation occurs by the reaction of saturated and/or unsaturated $C_4$-hydrocarbons, with an oxygen-containing gas and water vapor in the presence of at least one catalyst. The gas leaving the reactor is partly recirculated in a reaction gas circuit. This reaction gas circuit is configured such that part of the organic acids formed in the gas-phase oxidation is taken from the gas leaving the reactor, so that the acid content of the recirculated part of the gas leaving the reactor is from 0.01% to 6.0% by volume.

The saturated or unsaturated hydrocarbons having 4 carbon atoms are compounds selected from the group consisting of n-butane, i-butane, 1-butene, cis-2-butene, trans-2-butene, isobutene and 1,3-butadiene. Preference is given to n-butane and the butene isomers 1-butene, trans-2-butene and cis-2-butene and also mixtures comprising high proportions of these compounds. In the process of the invention, the $C_4$-hydrocarbon fraction can further comprise linear and/or branched and/or cyclic hydrocarbons having more or less than 4 carbon atoms, for example methane, ethane, ethene, propene, propane, pentanes, pentenes, pentadienes, cyclopentane, cyclopentene, cyclopentadiene and methylcyclopentane. Likewise, alcohols, aldehydes, ethers, ketones and esters having from 1 to 8 carbon atoms may be present. Preferred starting materials are cheap feedstock mixtures from petrochemical processing, e.g. "$C_4$ fraction" (predominantly butadiene and i-butene), "raffinate 1" (predominantly i-butene and n-butenes) and "raffinate 2" (predominantly butanes, 1-butene and 2-butenes) or mixtures comprising such hydrocarbons. These can, if desired, be used after a pretreatment, e.g. a purification or hydrogenation.

The reaction temperature in the gas-phase oxidation is generally from 100° C. to 400° C., preferably from 150° C. to 250° C., particularly preferably from 180° C. to 230° C. The reaction is generally carried out at pressures of from $1.2 \times 10^5$ Pa to $51 \times 10^5$ Pa, preferably from $4 \times 10^5$ Pa and $31 \times 10^5$ Pa, particularly preferably from $9 \times 10^5$ and $17 \times 10^5$ Pa.

As oxygen-containing gas, it is possible to use air, air enriched with oxygen and preferably pure oxygen. An inert gas such as nitrogen can also be present in the process of the invention.

The proportion by volume of water vapor in the reactor inlet gas consisting of water vapor, oxygen-containing gas, $C_4$-hydrocarbons and inert gases fed to the reactor is generally from 5% to 80% by volume, preferably from 5% to 40% by volume, particularly preferably from 5% to 30% by volume.

The proportion of butene, which may be present as starting material either alone or in admixture with further $C_4$-hydrocarbons, is from 1% to 5% by volume, preferably from 1.5% to 3% by volume. The proportion of butane, which likewise can be present as starting material either alone or in admixture with further $C_4$-hydrocarbons, is from 5% to 80% by volume, preferably from 5% to 60% by volume, particularly preferably from 10% to 50% by volume.

The oxygen content of the reactor inlet gas is from 1% to 35% by volume, preferably from 2% to 20% by volume, particularly preferably from 3% to 12% by volume.

In another embodiment, a proportion of inert gas of from 0% to 25% by volume can be fed in. The proportion of carbon oxides and further reaction by-products in the reactor inlet gas depends on the reaction procedure and the separation of acids. This is generally from 10% to 80% by volume, preferably from 15% to 65% by volume. The percentages by volume of the individual constituents of the reactor inlet gas in each case add up to 100% by volume.

Suitable catalysts for the process of the invention are all catalysts which have been generally described for the partial oxidation of saturated and/or unsaturated $C_4$-hydrocarbons to acetic acid. Preference is given to mixed oxide catalysts comprising the vanadium oxides; and particular preference is given to coated catalysts as are described in DE-A 19,649,426. The disclosure of DE-A 1 9,649,426 is herewith incorporated by reference into the present application. This catalyst is a coated catalyst comprising an inert nonporous support body and a catalytically active amount of a mixed oxide composition applied to the outer surface of the support body. The catalytically active composition comprises (a) one or more oxides selected from the group consisting of titanium dioxide, zirconium dioxide, tin dioxide and aluminum oxide and (b) from 0.1% to 1.5% by weight, based on the weight of the component (a) and per $m^2/g$ of specific surface area of the component (a), of vanadium pentoxide.

As additional component (a), it is possible for one or more oxides selected from the group consisting of oxides of boron, silicon, hafnium, niobium, tungsten, lanthanum and cerium to be present. If the component (a) is doped with the oxides specified, they are generally present in an amount of from 1% to 30% by weight, based on the total weight of the component (a).

In the component (b), it is possible, if desired, for part of the vanadium pentoxide, preferably from 10% to 90% by weight, to be replaced by one or more oxides of molybdenum, chromium and antimony. If desired, one or more oxides of alkali metals, elements of main groups V and VI of the Periodic Table of the Elements and the transition metals may also be present as additional component (b). In general, the amount of these dopants is from 0.005% to 15% by weight, calculated as oxides and based on the total weight of the component (b).

Preference is given to compositions having a high surface area of the component (a) of from 40 to 300 $m^2/g$, with tin oxide, niobium oxide or tungsten oxide being able to be present if desired, and having a component (b) which is doped with Mo and/or Cr and/or Sb and/or Au. The catalytically active mixed oxide composition may, if desired, also contain from 10% to 50% by weight, based on the total weight of the catalytically active mixed oxide composition, of inert diluents such as silicon dioxide, silicon carbide and graphite.

The catalytically active mixed oxide composition is applied as a shell to the outer surface of the support body in an amount of from 1% to 40% by weight, preferably from 5% to 25% by weight, in each case based on the total weight of support body and active composition. The thickness of the layer is generally from 10 to 2000 $\mu$m, preferably from 100 to 1000 $\mu$m. The coated catalyst may also comprise a plurality of layers having different compositions. It is also possible for one or more constituents of the active components (a) and (b) to be present in different concentrations in the individual layers.

Suitable materials for the inert, nonporous support body are all nonporous materials which are inert under the operating conditions of the gas-phase oxidation and are stable over the operating period. Examples are steatite, Duranit, silicon carbide, magnesium oxide, silicon oxide, silicates, aluminates, metals such as stainless steel and also, if desired, mixtures of these materials. Preference is given to ceramic materials such as steatite. The inert, nonporous support body can have any desired shape. Examples of suitable shapes are spheres, cylinders, cuboids, tori, saddles, spindles and helices. Likewise suitable as support are ordered packings such as monoliths or cross-channel structures. Preference is given to support shapes having as high as possible a geometric surface area per unit volume, for example rings.

The dimensions of the support bodies are determined by the reactors for the gas-phase oxidation. In general, the shaped bodies have a length or a diameter of from 2 to 20 mm. The wall thickness, for example in the case of rings or hollow cylinders, is advantageously from 0.1 to 4 mm.

In the process of the invention, the reaction gas circuit is configured such that part of the organic acids, primarily formic acid and acetic acid, present in the gas leaving the reactor is taken from this gas so that the partial pressure of these acids at the reactor inlet remains low. In general, the proportion of acid is reduced to from 0.01% to 6% by volume, preferably from 0.1% to 3% by volume, particularly preferably from 0.2% to 2% by volume. Unreacted $C_4$-hydrocarbons and intermediates such as acetaldehyde, acetone, methyl ethyl ketone and 2-butanol which can be reacted further to form acetic acid mostly remain in the circulated gas and are returned to the reactor inlet.

The process of the invention can be used to reduce the acid content to the abovementioned residual acid content in part of the gas leaving the reactor, generally from 60% to 99.8% by weight, preferably from 90% to 99.5% by weight. Subsequently, this part of the reactor outlet gas is recirculated to the reactor. The untreated part of the reactor outlet gas is then discarded and can, for example, be flared off. The proportion of untreated reactor outlet gas depends on the amount of carbon oxides $CO_x$ formed because these have to be discharged via this branch stream. They can then be disposed of by incineration.

An alternative embodiment of the process of the invention is to reduce the acid content of the reactor outlet gas to the abovementioned residual content immediately after the gas has left the reactor. Then the treated reactor outlet gas is recirculated to the reactor either completely or partially. It is preferably recirculated to an extent of from 60% to 99.8% by weight, particularly preferably from 90% to 99.5% by weight. This embodiment is particularly preferred since the target products, viz. the carboxylic acids, are substantially separated off beforehand and are not incinerated.

The organic acids can be separated off by known methods or a combination of these methods. Examples of suitable methods are partial condensation of the gas mixture; rectification, with or without addition of auxiliaries (e.g. extractive rectification); absorption of the acids in a suitable solvent; separation by means of a membrane and absorption by a solid absorbent. Preference is given to separating off the organic acids by means of partial condensation of the gas mixture, for example in a condenser, and subsequently dividing the remaining gas mixture.

The mass flow of recirculated gas is generally from 1 to 100 times, preferably from 5 to 80 times, particularly preferably from 10 to 40 times, the mass flow of fresh starting materials fed in.

The crude acid which has been separated off is dewatered and purified using suitable customary methods either alone or in combination, e.g. liquid—liquid extraction, extractive rectification, azeotropic rectification and rectification. The process of the invention is preferably used for preparing acetic acid and formic acid, particularly preferably acetic acid. An important advantage of the process of the invention is that in the preparation of acetic acid the by-products formed are obtained as useful materials, especially in the form of formic acid. In contrast, in the processes known from the prior art the formic acid formed as an intermediate is decomposed to form COX compounds which have to be disposed of by incineration.

As the reactor, it is possible to use apparatus embodiments which are suitable for carrying out oxidation reactions in the gas phase and are able to remove the high heat of reaction without excessive heating of the reaction mixture. The process of the invention can be carried out continuously or intermittently, i.e. a constant reactor inlet mixture can be fed in or the feed composition can vary cyclically. The gas mixture can react over a catalyst in a fixed bed, for example in a multitube reactor or tray reactor, or in a moving or fluidized bed. Preference is given to cooled multitube reactors containing a fixed catalyst bed. Particular preference is given to embodiments in which the individual tubes making up the multitube reactor have an internal diameter of from 10 mm to 50 mm and a length of from 1 m to 6 m. The flow velocity (based on the empty tube) in the reaction tubes is generally from 0.1 m/s to 10 m/s, preferably from 0.3 m/s to 5 m/s, particularly preferably from 0.5 to 3 m/s.

The reaction tubes can be charged with catalysts having different compositions, shapes and dimensions. The charge can have been introduced into the reaction tubes so as to be homogeneous or vary zonewise in the axial direction. Each zone can contain randomly diluted or mixed catalysts.

BRIEF DESCRIPTION OF THE DRAWINGS

Other objects and features of the present invention will become apparent from the following detailed description considered in connection with the following examples and the accompanying drawings which disclose several embodiments of the present invention. It should be understood, however, that the examples and drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
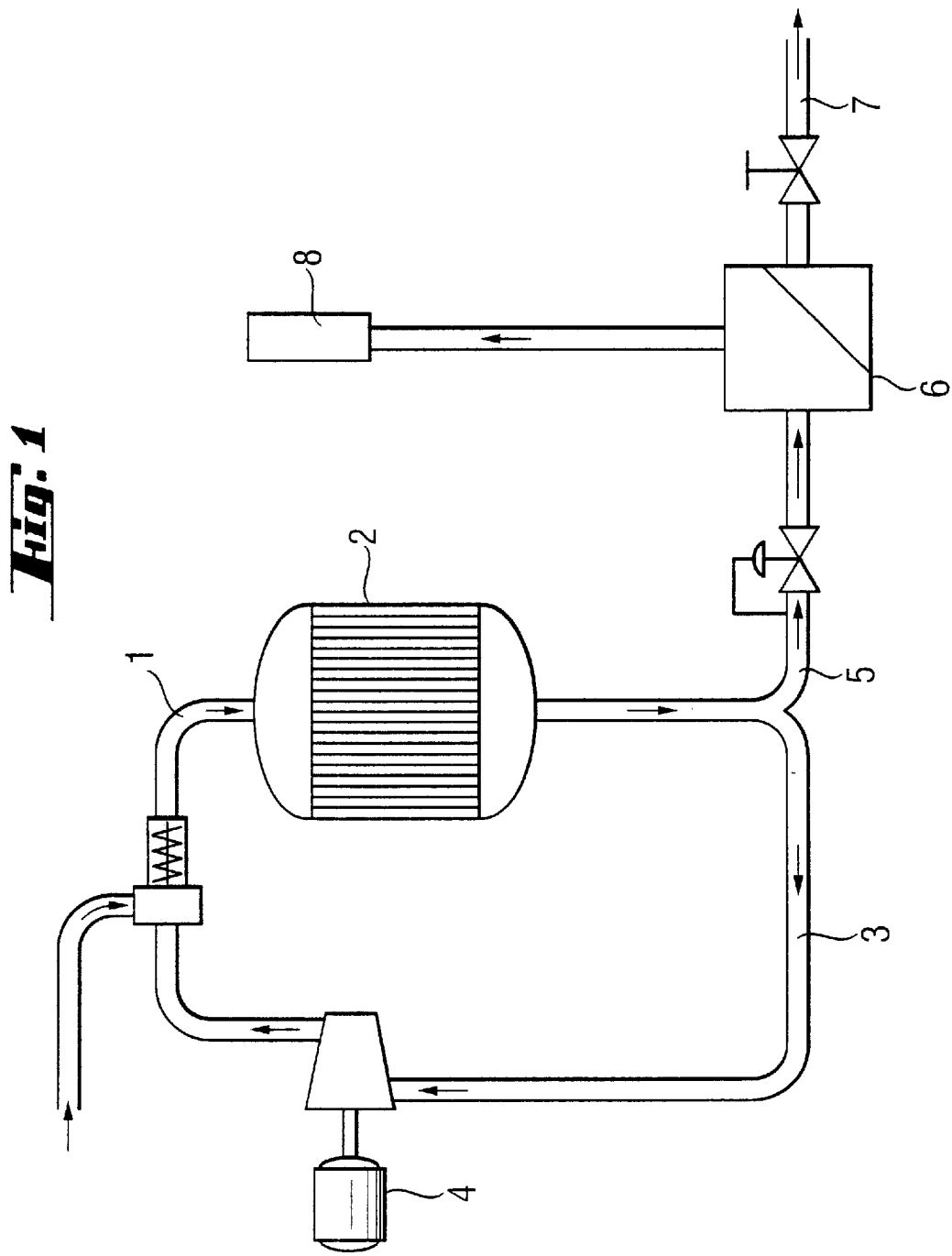
FIG. 1 shows an apparatus according to the prior art.

Turning now in detail to the drawings, FIG. 1 shows an apparatus according to the prior art. Here, the reactor inlet gas is fed via the feed line (1) to a reactor (2). Part of the gas mixture leaving the reactor goes through pipe (5) to the separation apparatus (6), for example a cooler with downstream phase separator. The acid is isolated by partial condensation and drained off via line (7) and the remaining gas is conveyed to incineration (8). The other part of the reactor outlet gas is recirculated to the reactor inlet via pipe (3), without separation of acid, by means of a gas conveying device (4), for example a blower.

Figure 2:
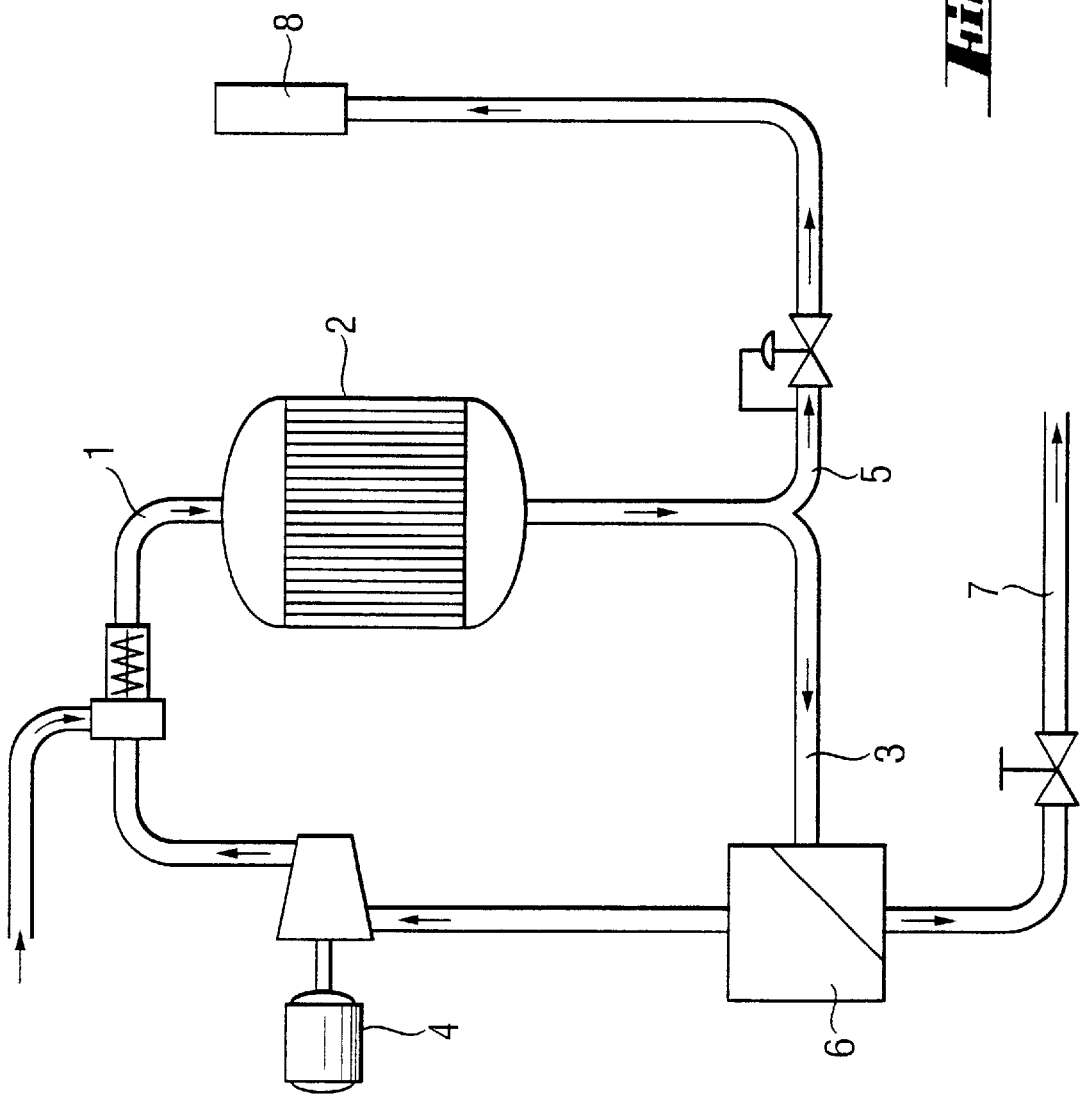
FIG. 2 shows an apparatus according to the invention.

FIG. 2 shows an apparatus according to the invention, in which the acid is separated off in the return stream. Here, the reactor inlet gas is fed via the feed line (1) to a reactor (2). From this reactor, the major part of the reactor outlet gas goes through pipe (3) to the separation apparatus (6), for example a cooler with downstream phase separator. The major part of the acid is isolated by partial condensation and drained off via line (7). The volatile remainder is recirculated to the reactor inlet by means of a gas conveying device (4) which may be a blower or a compressor. Excess gas obtained in the regulation of the pressure goes through pipe (5) to incineration (8).

Figure 3:
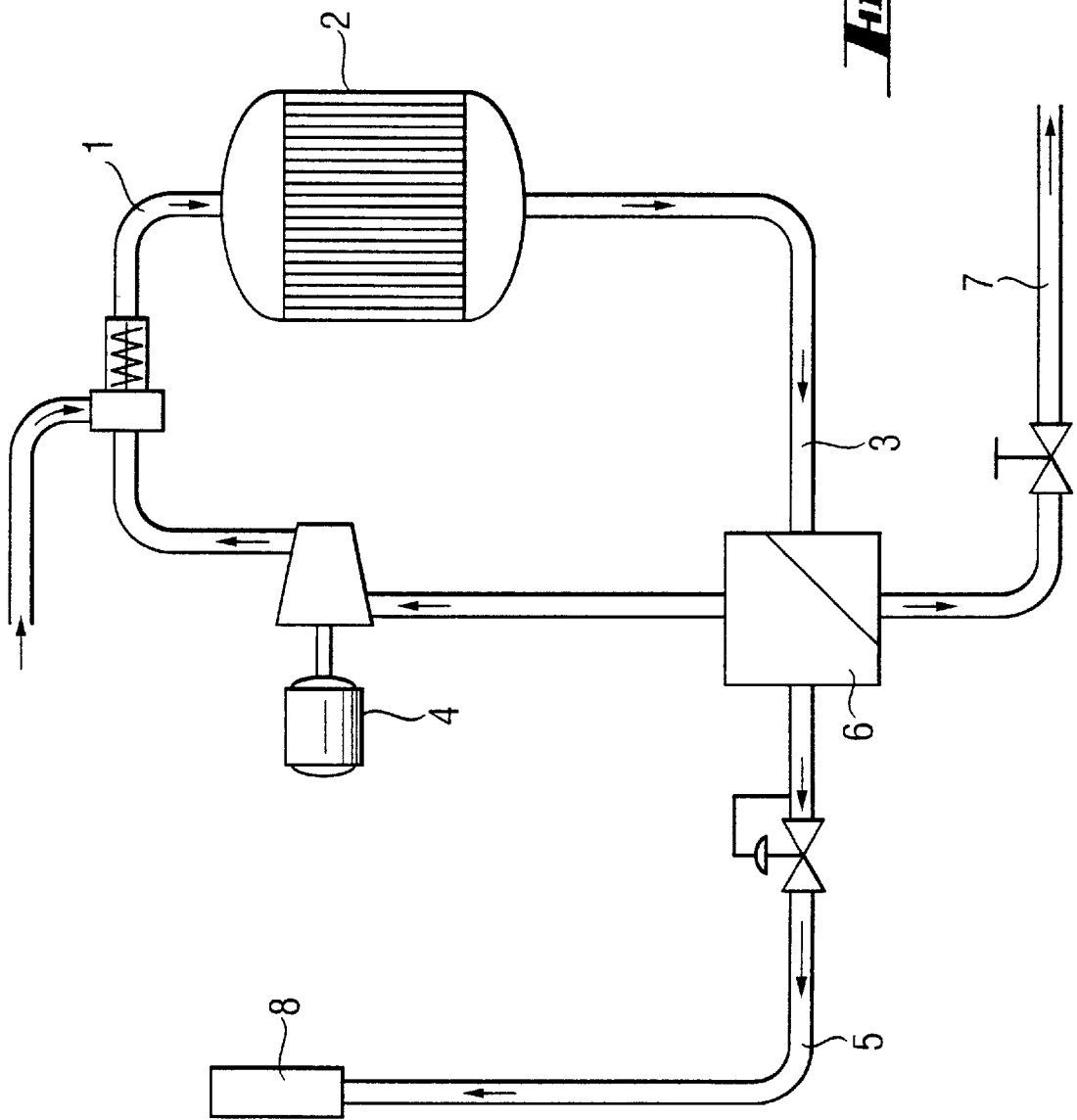
FIG. 3 shows a second embodiment of an apparatus according to the invention.

FIG. 3 shows another embodiment of the apparatus according to the invention, in which the acid is separated off directly at the outlet from the reactor before the gas stream is divided. Here, the reactor inlet gas is fed via the feed line (1) to a reactor (2). From this reactor, the reactor outlet gas goes via line (3) to the separation apparatus (6), for example a cooler with downstream phase separator. The major part of the acid is isolated by partial condensation and drained off via line (7). The volatile remainder is recirculated to the reactor inlet by means of a gas conveying device (4) which may be a blower or a compressor. Excess gas obtained in the regulation of the pressure goes through pipe (5) via a pressure regulator to incineration (8).

The following examples illustrate the invention. The yield [mol %] was calculated as follows: moles of carbon in the product/moles of carbon in the starting material used×100 gives the reaction yield.

The reactor dimensions are as follows. In Examples 1 to 4 and in the Comparative Examples, the tube reactor has an internal diameter of 19 mm and has a length of 6 m. In Example 5, the tube reactor has an internal diameter of 25 mm and has a length of 6 m.

Regarding the catalysts, in Examples 1, 2 and in the Comparative Examples 1 to 3, the catalyst utilized was a coated catalyst having an active composition comprising oxides of titanium, vanadium, molybdenum and antimony. A specific example of the catalyst used was one having the empirical formula $Ti_aV_bMo_cSb_dO_e$ (a: 93; b: 7.4; c: 1, d: 2.8; e: 211). This catalyst was applied in an amount of 18% by weight, based on the total weight of the support, to steatite rings support having the dimensions: external diameter=7 mm, internal diameter=4 mm, height=4 mm.

In Examples 3 and 4, the catalyst utilized was a coated catalyst having an active composition comprising oxides of titanium, vanadium and antimony. A specific example of the catalyst used was one having the empirical formula $Ti_aV_bSb_dO_e$ (a: 11.8; b: 1, d: 1.18; e: 27.8). This catalyst was applied in an amount of 13.5% by weight with the addition of 1.5% by weight of graphite, in each case based on the total weight of the support, to steatite rings support having the dimensions: external diameter=7 mm, internal diameter=4 mm, height=4 mm.

In Example 5, the catalyst utilized was a coated catalyst having an active composition comprising oxides of titanium, vanadium and antimony. A specific example of the catalyst used was one having the empirical formula $Ti_aV_bSb_dO_e$ (a: 11.8; b: 1; d: 1.18; e: 27.8). This catalyst was applied in an amount of 10.8% by weight with the addition of 1.2% by weight of graphite, in each case based on the total weight of the support, to steatite rings support having the dimensions: external diameter=7 mm, internal diameter=4 mm, height=7 mm.

EXAMPLE 1 (Invention)
(Circulating Gas Method with Separation of Acid as Shown in FIG. 2)

A tube reactor having an internal diameter of 19 mm and a length of 6 m which was equipped with a heating device and had been charged with the above-described catalyst was supplied at a pressure of $7 \times 10^5$ Pa and a temperature of 190° C. with 600 g/h of water, 250 g/h of oxygen and 120 g/h of 1-butene.

The gas mixture leaving the reactor was divided. A substream of 60 g/h was fed to a scrubber and was subsequently flared off. The remaining 9000 g/h of the reactor outlet gas was partially condensed at 70° C. in a cooler and the liquid fraction comprising the acetic acid was isolated in a phase separator and the remaining gas was recirculated to the reactor inlet. The proportion of acid in the recirculated gas was thus reduced to 1.2% by volume. Under these conditions, a butene conversion of 99.5% was achieved. The acetic acid yield was 71 mol %, the acetaldehyde yield was 0.5 mol % and the formic acid yield was 9 mol %. The space-time output was 107 g of acetic acid per liter of catalyst and hour. The crude acid concentration was 25% by weight.

EXAMPLE 2 (Invention)
(Circulating Gas Method with Separation of Acid as Shown in FIG. 2)

The procedure of Example 1 was repeated with the reactor being supplied with 600 g/h of water, 31 g/h of nitrogen, 250 g/h of oxygen and 120 g/h of 1-butene. The gas mixture leaving the reactor was divided. A substream of 90 g/h was fed to a scrubber and was subsequently flared off. The remaining 9000 g/h of the reactor outlet gas were partially condensed at 70° C. in a cooler. The liquid fraction comprising the acetic acid was isolated in a phase separator and the remaining gas was recirculated to the reactor inlet. The proportion of acid in the recirculated gas was thus reduced to 1.2% by volume.

Under these conditions, a butene conversion of 98% was achieved. The acetic acid yield was 66 mol %, the acetaldehyde yield was 0.5 mol % and the formic acid yield was 8.5 mol %. The space-time output was 99 g of acetic acid per liter of catalyst and hour. The crude acid concentration was 23% by weight.

COMPARATIVE EXAMPLE 1
(Single Pass Through the Reactor)

The tube reactor from Example 1 was supplied at $5 \times 10^5$ Pa and 205° C. with 1600 g/h of water, 390 g/h of nitrogen, 130 g/h of oxygen and 113 g/h of 1-butene. The reactor outlet gas was not circulated but was divided after passage through the reactor.

Under these conditions, a butene conversion of 50% was achieved. The acetic acid yield was 34 mol %, the acetaldehyde yield was 5 mol % and the formic acid yield was 2 mol %. The space-time output was 48 g of acetic acid per liter of catalyst and hour. The crude acid concentration was 5% by weight.

COMPARATIVE EXAMPLE 2
(Circulating Gas Method without Separation of Acid)

The procedure of Example 1 was repeated but the reactor was supplied at a pressure of $4 \times 10^5$ Pa and a temperature of 220° C. with 200 g/h of water, 143 g/h of oxygen and 130 g/h of 1-butene. 4700 g of the reactor outlet gas were, without separation of acid, recirculated directly to the reactor inlet and 460 g/h of the reactor outlet gas were taken off for product recovery and discharge of carbon oxides from the circulating gas system.

Under these conditions, a butene conversion of 60% was achieved. The acetic acid yield was 36 mol %, the acetaldehyde yield was 1.2 mol % and the formic acid yield was 1.2 mol %. The space-time output was 60 g of acetic acid per liter of catalyst and hour. The crude acid concentration was 30% by weight.

COMPARATIVE EXAMPLE 3
(Circulating Gas Method without Separation of Acid)

The procedure of Comparative Example 2 was repeated but the reactor was supplied at $7 \times 10^5$ Pa and 190° C. with 200 g/h of water, 490 g/h of nitrogen, 170 g/h of oxygen and 130 g/h of 1-butene. 9100 g of the reactor outlet gas were, without separation of acid, recirculated directly to the reactor inlet and 990 g/h of the reactor outlet gas were taken off for product recovery and discharge of carbon oxides from the circulating gas system.

Under these conditions, a butene conversion of 46% was achieved. The acetic acid yield was 29 mol %, the acetaldehyde yield was 3.2 mol % and the formic acid yield was 2.3 mol %. The space-time output was 50 g of acetic acid per liter of catalyst and hour. The crude acid concentration was 25% by weight.

EXAMPLE 3 (Invention)
Circulating Gas Method with Separation of Acid as Shown in FIG. 2)

The procedure of Example 1 was repeated using the abovementioned coated catalyst, but 700 g/h of water, 310 g/h of oxygen, 120 g/h of 1-butene and 80 g/h of n-butane were fed to the reactor at $11\times10^5$ Pa and 200° C. The gas mixture leaving the reactor was divided. A substream of 70 g/h was fed to a scrubber and was subsequently flared off. The remaining 18000 g/h of the reactor outlet gas were partially condensed at 60° C. in a cooler. The liquid fraction comprising the acetic acid was isolated in a phase separator and the remaining gas was recirculated to the reactor inlet. The proportion of acid in the recirculated gas was thus reduced to 0.5% by volume.

Under these conditions, a butene conversion of 99.5% and a butane conversion of 68% was achieved. The acetic acid yield was 50 mol % and the formic acid yield was 5 mol %. The space-time output was 120 g of acetic acid per liter of catalyst and hour. The crude acid concentration was 25% by weight.

EXAMPLE 4 (Invention)
(Circulating Gas Method with Separation of Acid as Shown in FIG. 2)

The procedure of Example 3 was repeated using the above-mentioned coated catalyst, but 700 g/h of water, 136 g/h of oxygen and 120 g/h of n-butane were fed to the reactor at $11\times10^5$ Pa and 205° C. The gas mixture leaving the reactor was divided. A substream of 90 g/h was fed to a scrubber and was subsequently flared off. The remaining 20000 g/h of the reactor outlet gas were partially condensed at 60° C. in a cooler. The liquid fraction comprising the acetic acid was isolated in a phase separator and the remaining gas was recirculated to the reactor inlet. The proportion of acid in the recirculated gas was thus reduced to 0.4% by volume.

Under these conditions, a butane conversion of 53% was achieved. The acetic acid yield was 34 mol % and the formic acid yield was 3 mol %. The space-time output was 50 g of acetic acid per liter of catalyst and hour. The crude acid concentration was 12% by weight.

EXAMPLE 5 (Invention)
(Circulating Gas Method with Separation of Acid as Shown in FIG. 3)

A reactor having an internal reaction tube diameter of 25 mm and a reactor length of 600 cm which was equipped with a heating device. This reactor was charged with the above-mentioned catalyst and was supplied at a pressure of $11\times10^5$ Pa and at 198° C. with 700 g/h of water, 310 g/h of oxygen, 120 g/h of 1-butene and 120 g/h of n-butane.

The acid was separated off by partial condensation at 65° C., thus lowering the proportion of acid in the reactor outlet gas to 0.65% by volume. 98% by weight of the uncondensed gas after separation of the acid were recirculated to the reactor, thus resulting in a circulating gas flow of 10,000 g/h. The remainder, viz. 200 g/h, of the uncondensed gas after separation of the acid was fed to waste gas incineration.

Under these conditions, a butene conversion of 98% and a butane conversion of 20% were achieved. The acetic acid yield was 42 mol %, the acetaldehyde yield was 0.5 mol % and the formic acid yield was 4 mol %. The space-time output was 73 g of acetic acid per liter of catalyst and hour. The crude acid concentration was 24% by weight.

The result from the Examples (Invention) and Comparative Examples are summarized in Table 1.

TABLE 1

| Example | Butene conversion (%) | Butane conversion (%) | Acetic acid (mol %) | Acetaldehyde (mol %) | Formic acid (mol %) | Space-time output (g/l) | Crude acid (% by wt.) |
|---|---|---|---|---|---|---|---|
| Ex. 1 | 99.5 | | 71 | 0.5 | 5 | 107 | 25 |
| Ex. 2 | 98 | | 66 | 0.5 | 8.5 | 99 | 5 |
| C. Ex. 1 | 50 | | 34 | 5.0 | 2 | 48 | 5 |
| C. Ex. 2 | 60 | | 36 | 1.2 | 1.2 | 60 | 30 |
| C. Ex. 3 | 46 | | 29 | 3.2 | 2.3 | 50 | 25 |
| Ex. 3 | 99.5 | 68 | 50 | | 5 | 120 | 25 |
| Ex. 4 | | 53 | 34 | | 3 | 50 | 12 |
| Ex. 5 | 98 | 20 | 42 | 0.5 | 4 | 73 | 24 |

Accordingly, while a few embodiments of the present invention have been shown and described, it is to be understood that many changes and modifications may be made thereunto without departing from the spirit and scope of the invention as defined in the appended claims.

What is claimed is:

1. An apparatus for preparing saturated carboxylic acids having from 1 to 4 carbon atoms comprising
   a reactor (2) which is provided with an input feed line (1) and an outlet pipe (5) for separating off excess gas; and said reactor being selected from the group consisting of a tube reactor, a multitube reactor, and a tray reactor;
   a pipe (3) for connecting said reactor (2) to a separation means (6) for partially condensing or separating off said acids; and said separation means being selected from the group consisting of a partial condenser, a rectification means, means for absorption in a solvent, a membrane separation means, and a solid absorbent means;
   means for connecting the separation means (6) to the input feed line (1); and a catalyst in said rector; and said catalyst being present selected from the group consisting of in a fixed bed, in a moving bed, and a fluidized bed;

and wherein the catalyst used is a coated catalyst comprising an inert nonporous support body; and said support body having an outer surface; and a catalytically active mixed oxide composition comprising (a) one or more oxides selected from the group consisting of titanium dioxide, zirconium dioxide, tin dioxide and aluminum oxide and (b) from 0.1% to 1.5% by weight, based on the weight of the component (a) and per $m^2/g$ of specific surface area of the component (a), of vanadium pentoxide applied to said outer surface of the support body.

2. An apparatus for preparing saturated carboxylic acids having from 1 to 4 carbon atoms comprising a reactor (2) having an input feed line (1); and said reactor being selected from the group consisting of a tube reactor, a multitube reactor, and a tray reactor;

a pipe (3) for connecting the reactor (2) directly to a separation means (6); and said separation means being selected from the group consisting of a partial condenser, a rectification means, means for absorption in a solvent, a membrane separation means, and a solid absorbent means;

a pipe (5) for discharging excess gas from the separation means (6); and means for connecting the separation means (6) to the input feed line (1); and a catalyst in said reactor; and said catalyst being present selected from the group consisting of a fixed bed, in a moving bed, and in a fluidized bed;

wherein the catalyst used is a coated catalyst comprising an inert nonporous support body; and said support body having an outer surface; and a catalytically active mixed oxide composition comprising (a) one or more oxides selected from the group consisting of titanium dioxide, zirconium dioxide, tin dioxide and aluminum oxide and (b) from 0.1% to 1.5% by weight, based on the weight of the component (a) and per $m^2/g$ of specific surface area of the component (a), of vanadium pentoxide applied to said outer surface of the support body.

3. An apparatus as claimed in claim 1, wherein the reactor used is a tube reactor.

4. An apparatus as claimed in claim 1, wherein the tube reactor used is a multitube reactor.

5. An apparatus as claimed in claim 1, wherein the catalyst is present in the reactor as a fixed bed.

6. An apparatus as claimed in claim 1, wherein the separation means is a partial condenser.

7. An apparatus as claimed in claim 2, wherein the reactor used is a tube reactor.

8. An apparatus as claimed in claim 2, wherein the tube reactor used is a multitube reactor.

9. An apparatus as claimed in claim 2, wherein the catalyst is present in the reactor as a fixed bed.

10. An apparatus as claimed in claim 2, wherein the separation means is a partial condenser.

* * * * *